US00PP33033P2

(12) United States Plant Patent
Smit

(10) Patent No.: US PP33,033 P2
(45) Date of Patent: May 4, 2021

(54) ***PEPEROMIA* PLANT NAMED 'EC-PEPE-1903'**

(50) Latin Name: *Peperomia vestita*
Varietal Denomination: EC-PEPE-1903

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 16/873,174

(22) Filed: Feb. 18, 2020

(51) Int. Cl.
*A01H 5/12* (2018.01)

(52) U.S. Cl.
USPC ..... Plt./373

(58) Field of Classification Search
USPC ..... Plt./373
CPC ..... A01H 5/12; A10H 6/00
See application file for complete search history.

*Primary Examiner* — Keith O. Robinson
(74) *Attorney, Agent, or Firm* — Cassandra Bright

(57) ABSTRACT

A new and distinct cultivar of *Peperomia* plant named 'EC-PEPE-1903' is disclosed, characterized by large, velvety, oval-shaped leaves with greyed-orange petioles. The new variety is a *Peperomia*, typically used as an ornamental plant.

2 Drawing Sheets

Figure 1:
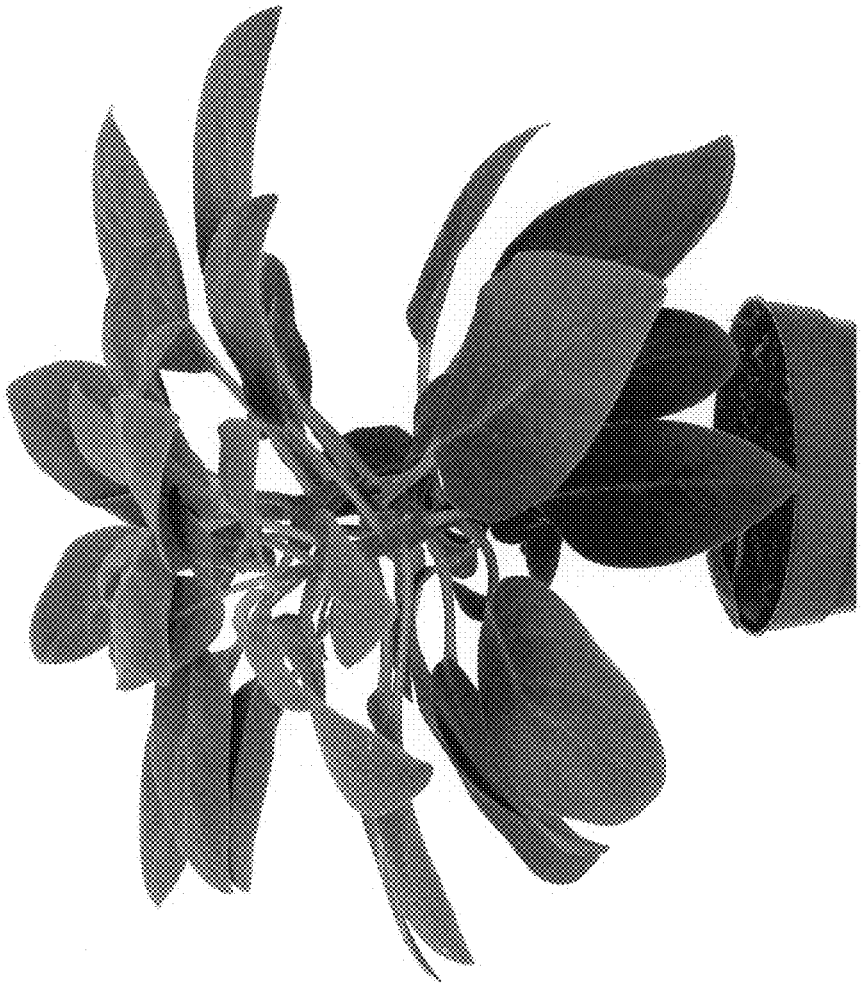

Latin name of the genus and species: *Peperomia vestita*.
Variety denomination: 'EC-PEPE-1903'.

BACKGROUND OF THE INVENTION

The new cultivar is a product of a planned breeding program. The new variety was selected as a seedling resulting from the crossing of two unnamed, unpatented varieties of *Peperomia vestita*. The crossing was made by the inventor, Obed J. Smit, a citizen of the Netherlands in 2014. 'EC-PEPE-1903' was selected by the inventor in 2017 at a commercial greenhouse in Sappemeer, the Netherlands.

Asexual reproduction of the new cultivar 'EC-PEPE-1903' by terminal cuttings was first performed in Sappemeer, the Netherlands at a commercial greenhouse in March 2017 and has shown that the unique features of this cultivar are stable and reproduced true to type through successive generations.

SUMMARY OF THE INVENTION

The cultivar 'EC-PEPE-1903' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-1903'. These characteristics in combination distinguish 'EC-PEPE-1903' as a new and distinct *Peperomia* cultivar:

1. Thick, rigid stems occurring at a very acute, near vertical angle.
2. Oval-shaped leaves with greyed-orange petioles.
3. Pubescent leaves with velvety soft touch.

PARENT COMPARISON

Plants of the new cultivar 'EC-PEPE-1903' are similar to plants of the female parent in most horticultural characteristics, however, plants of the new cultivar 'EC-PEPE-1903' differ from in the following characteristics:

1. Petioles of the new variety are a greyed-orange color, while petioles of the seed parent are green.
2. The new variety has a strong, rigid stem, while the seed parent has a weak stem.

Plants of the new cultivar 'EC-PEPE-1903' are similar to plants of the male parent in most horticultural characteristics, however, plants of the new cultivar 'EC-PEPE-1903' differ in the following characteristics:

1. Petioles of the new variety are a greyed-orange color, while petioles of the pollen parent are more red.
2. Leaves of the new variety are larger than leaves of the pollen parent.

COMMERCIAL COMPARISON

Plants of the new cultivar 'EC-PEPE-1903' are similar to plants of the commercial variety *Peperomia caperata* 'Eden Rosso', U.S. Plant Pat. No. 24,379. However, plants of the new cultivar differ in the following characteristics:

1. Leaf upper side of the new variety is a lighter green than that of this comparator.
2. Leaf under side of the new variety is light green, while leaf under side of this comparator is red.
3. Leaves of the new variety are much larger than this comparator.
4. New variety has an upright growth habit, while this comparator has a rosette growth habit.

Plants of the new cultivar 'EC-PEPE-1903' are similar to plants of the unnamed, unpatented *Peperomia obtusifolia*, grown commercially. However, plants of the new cultivar differ in the following characteristics:

1 The new variety has pubescent leaves, while this comparator has smooth leaves.
2. Leaves of the new variety are more elongated than leaves of this comparator.

3. Leaf placement of the new variety is opposite, while leaf placement of this comparator is staggered.

BRIEF DESCRIPTION OF THE PHOTOGRAPHS

The accompanying photograph in FIG. 1 illustrates in full color a typical blooming plant of 'EC-PEPE-1903' grown in a greenhouse. The plant is approximately 30 weeks of age.

Figure 2:
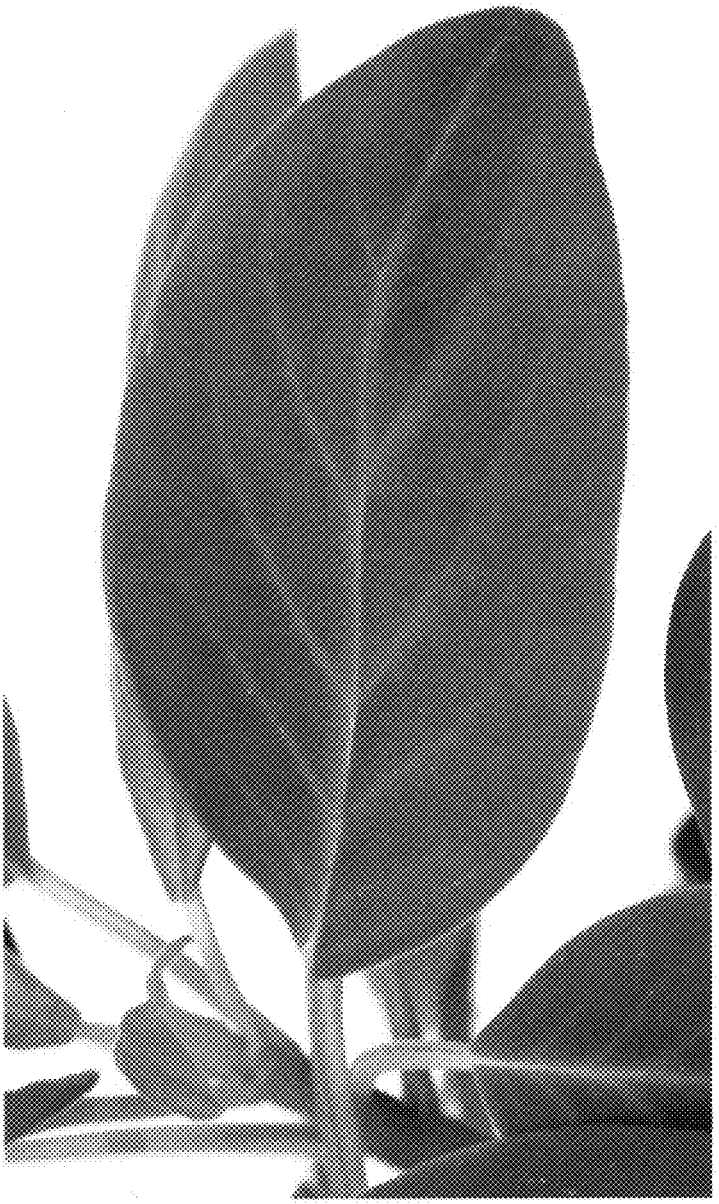

FIG. 2 illustrates a close up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-1903' plants at 22 weeks of age, grown in a greenhouse in Sappemeer, the Netherlands during August of 2019. The growing temperature ranged from 17° C. to 20° C. at night to 19° C. to 21° C. during the day. Measurements and numerical values represent averages of typical flowering types.

Botanical classification: *Peperomia vestita* 'EC-PEPE-1903'.

PROPAGATION

Time to initiate roots: About 21 days at approximately 20° C. in Summer.

Time to produce rooted cutting: About 25 days at 20° C. in Summer.

Description of roots: Herbaceous, fine, moderately dense, freely branching. White in color, not accurately measured with R.H.S. chart.

PLANT

Plant type: Upright, tender indoor foliage plant.

Plant shape: Broad, obovate.

Growth habit: Broad upright.

Plant spread: Approximately 41.8 cm.

Height: 31.8 cm to top of foliar plane.

Growth rate: Moderate.

Plant vigor: Moderate to high.

Age of plant described: Approximately 22 weeks from a rooted cutting.

Branching habit: A single main branch grows from the base, with lateral branches.

Pinching: Pinching will improve lateral branching.

Number of primary (main) branches per plant: Average 1.

Number of secondary (lateral) branches per plant: Average 2.

Lateral stems:

*Length*.—Average: 10.3 cm.

*Diameter*.—Average: 1.1 cm.

Internode length: Average: 0.9 cm.

Appearance and shape: Succulent, thick and rounded.

Luster: Moderately glossy.

Aspect/angle from vertical: Average angle: 15° (varying between 10° and 20°).

Strength: Strong.

Color:

*Developing*.—RHS Yellow-Green 144B.

*Mature*.—RHS Yellow-Green, between 143A and 144A.

*At internodes*.—RHS Yellow-Green 144B, between 143A and 144A.

*Bark/older stems*.—RHS Yellow-Green 148A to RHS Greyed-Green 197B.

Pubescence: Stems densely covered with very short soft hairs, average length less than 0.1 mm, colored green-white, too small to be measured with R.H.S. chart.

Plant fragrance: None observed.

FOLIAGE

Leaf:

*Arrangement*.—Alternate, single.

*Quantity*.—Average 14.

*Average length*.—14.7 cm.

*Average width*.—9 cm.

*Shape of blade*.—Ovate to broad ovate.

*Apex*.—Bluntly acute.

*Base*.—Short acuminate.

*Margin*.—Entire, densely pubescent with very short soft hairs, average length less than 0.1 mm, colored green-white, too small to be measured with R.H.S. chart.

*Aspect*.—Flat to slightly convex.

*Texture of top surface*.—Smooth, slightly leathery, soft to the touch due to pubescence.

*Texture of bottom surface*.—Smooth, slightly leathery, soft to the touch due to pubescence.

*Pubescence*.—Both sides densely pubescent with very short, soft hairs, average length less that 0.1 mm, colored green-white, too small to be measured with R.H.S. chart.

*Luster, upper side*.—Matte.

*Luster, under side*.—Moderately glossy.

*Color*.—Young foliage upper side: RHS Green 143A, and Green 141B. Young foliage under side: Near RHS Yellow-Green 147C. Mature foliage upper side: Between RHS Green NN137A and Yellow-Green 147A. Mature foliage under side: RHS Yellow-Green, between 146C and 147C.

*Venation*.—Type: Pinnate. Venation color upper side: RHS Yellow-Green 143A. Venation color under side: RHS Yellow-Green 145B.

*Petiole*.—Average Length: 6.8 cm. Diameter: 5 mm. Texture: Smooth, densely pubescent with very short, soft hairs, average length less than 0.1 mm, colored green-white, too small to be measured with R.H.S. chart. Strength: Medium. Color, upper side: RHS Greyed-Orange 173A, fading to Yellow-Green 144A to 144B towards proximal end. Color, under side: RHS Yellow-Green 144B.

FLOWER

No flowers observed to date.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures from approximately 10° C. to 35° C.

What is claimed is:

1. A new and distinct cultivar of *Peperomia* plant named 'EC-PEPE-1903' as herein illustrated and described.

* * * * *